United States Patent [19]

Oreopoulos et al.

[11] 4,215,690
[45] Aug. 5, 1980

[54] MEDICAL NEEDLE

[76] Inventors: Dimitrios G. Oreopoulos, 10 Ladywood Dr., Rexdale, Canada, M9V1K9; Gabor Zellerman, 588-590 Richmond St. W., Toronto, Canada, M5V 1Y9

[21] Appl. No.: 878,415

[22] Filed: Feb. 16, 1978

[51] Int. Cl.² .............................................. A61M 5/00
[52] U.S. Cl. .................................. 128/221; 128/214.4
[58] Field of Search ................. 128/221, 214.2, 214.4, 128/247, 218 R, 218 N

[56] References Cited
U.S. PATENT DOCUMENTS 2,845,068  7/1958  Gabriel .................................. 128/221
3,406,685  10/1968  May ..................................... 128/214.4
3,454,006  7/1969  Langdon ........................... 128/214.4

FOREIGN PATENT DOCUMENTS 790935  9/1935  France ..................................... 128/221

Primary Examiner—John D. Yasko
Attorney, Agent, or Firm—Fetherstonhaugh & Co.

[57] ABSTRACT

This invention relates to a tubular needle for making an interconnection between a vessel containing a fluid and a plastics tube that can be series connected with similar tubular needles so that each needle of the series can be maintained sterile until required for use. In use, needles in the series of connected needles are exposed for use one at a time as required.

6 Claims, 10 Drawing Figures

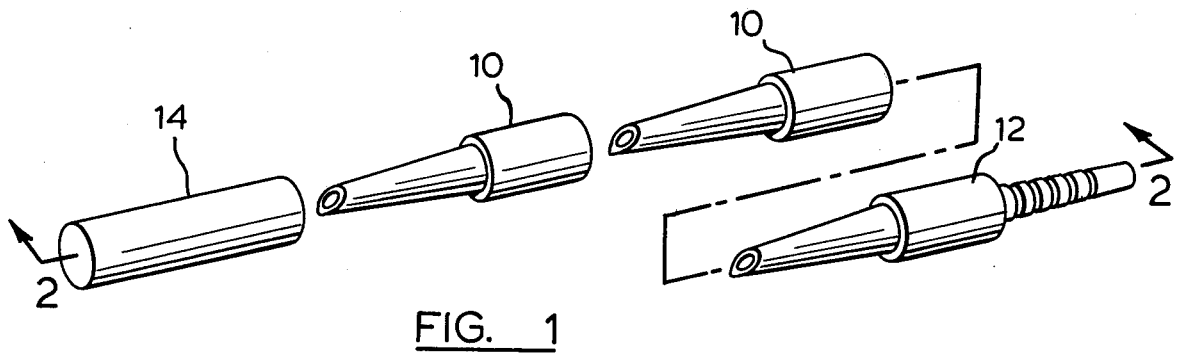
FIG. 1
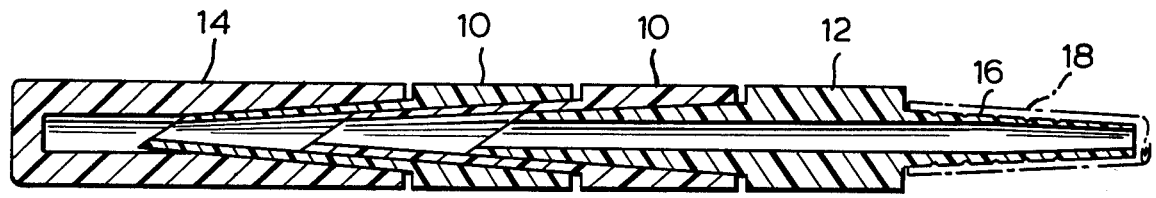
FIG. 2
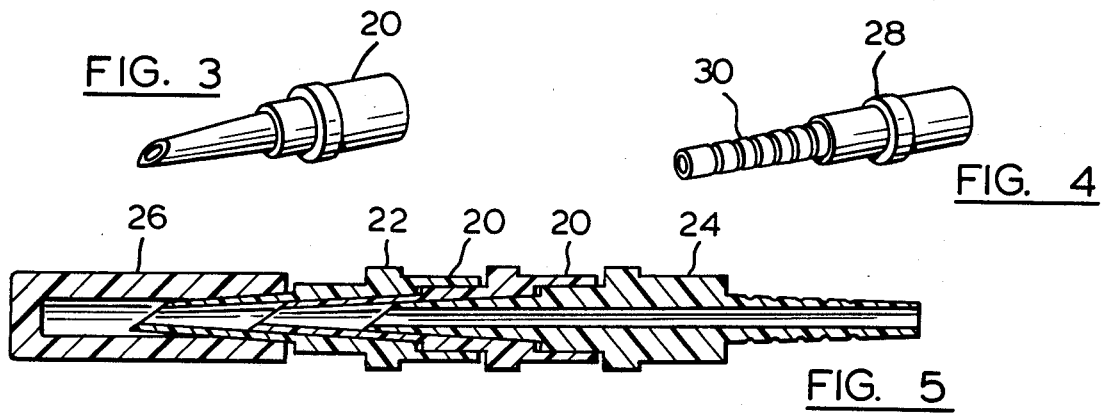
FIG. 3    FIG. 4
FIG. 5
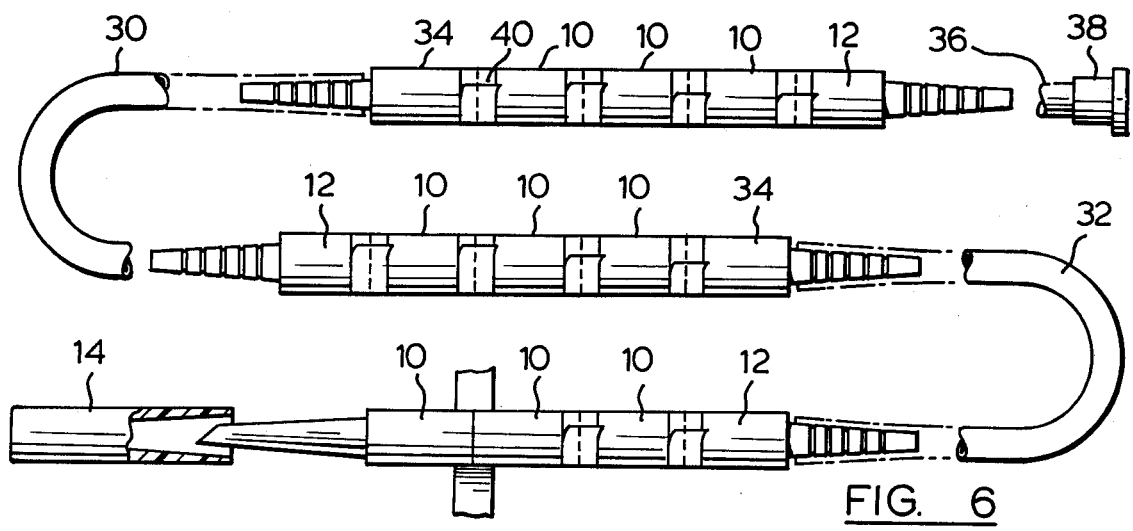
FIG. 6

MEDICAL NEEDLE

There are applications in the medical field where it is necessary to repeatedly make connections between the end of a tube and a vessel containing a fluid. For example, in the practice of a dialysis technique known as continuous ambulatory peritoneal dialysis (CAPD) a plastics material tube connects at one end with a catheter permanently implanted in the abdomen of the patient and must be connected at its other end to a container for dialysate. The container of dialysate must be changed frequently so that connection between the end of the tube and a dialysate container must be made and remade on a continuing basis.

The interconnection is commonly made with a needle attached to the end of the tube that will pierce a membrane in a neck of the dialysate container to make the interconnection. Sterility of the needle is of great importance in the successful practice of the technique and exposure of the needle as it is used is a source of contamination.

This invention relates to a needle that can be interconnected in a series with similar needles into a series so that a fresh needle can be used for each connection and one needle only of the series is exposed for use. After the exposed needle is used, it is discarded.

It is, therefore, an objection of the invention to provide a tubular needle design for connecting a hose to a container wherein a series of needles can be interconnected in a manner that one only of the series is exposed for use and each needle, as it is exposed, has a sterile front end for interconnection to a container.

With this and other objections in view, a tubular needle according to the invention comprises an elongated body with a through passage, said body having an inside wall, an outside wall, a front end and a back end, said through passage of said body adjacent said back end of said body having a cross section greater than the cross-section of said body adjacent said front end of said body whereby said tubular needle can be telescoped into a similar tubular needle by projecting said front end thereof into the back end of a similar needle, said outside wall of said wall being adapted to seat on the inside of said wall of a similar needle adjacent the front end thereof in fluid tight relation to limit the projection of said outside wall of said body into said back end of a similar needle as aforesaid.

In the drawings:

FIG. 1 is an illustration of a cap, two tubular needles that are adapted to telescope with respect to each other and a tubular needle that is adapted to telescope with respect to another tubular needle and also to connect to a flexible tube;

FIG. 2 is an illustration of the parts of FIG. 1 in telescoped relation and connected to a tube;

FIG. 3 is an illustration of a tubular needle of a different design;

FIG. 4 is an illustration of a fitting adapted to receive the front end of a tubular needle and to be connected to a flexible supply tube;

FIG. 5 is a cross sectional illustration of an assembly using needles of the design of FIGS. 3 and 4;

FIG. 6 is an illustration of an assembly of three series of tubular needles;

Figure 7:
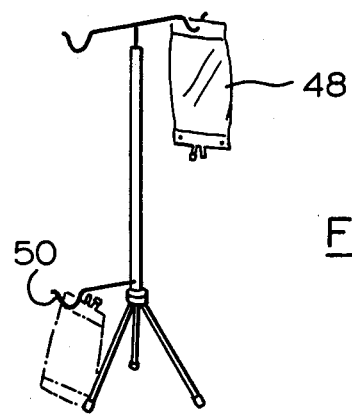
FIG. 7 is an illustration of a stand for holding dialysate bags in the practice of a dialysis technique known as continuous ambulatory peritoneal dialysis (CAPD)
Figure 8:
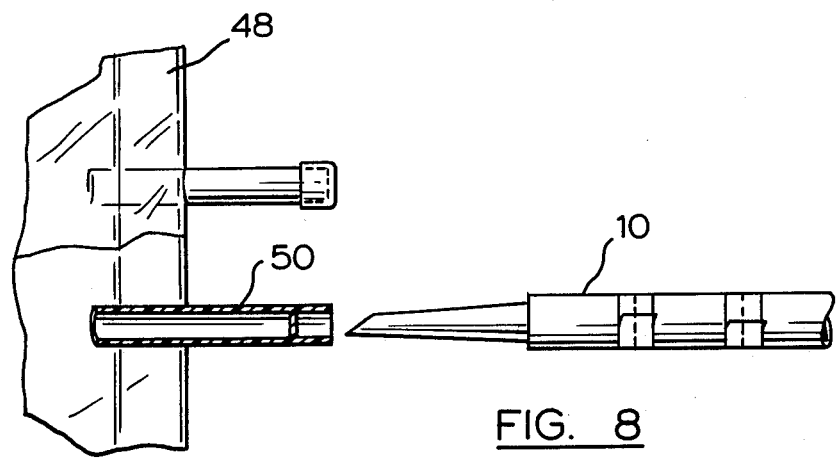
FIGS. 8 and 9 are views illustrating the manner in which the tubular needle described punctures the neck opening of a dialysate bag.
Figure 9:
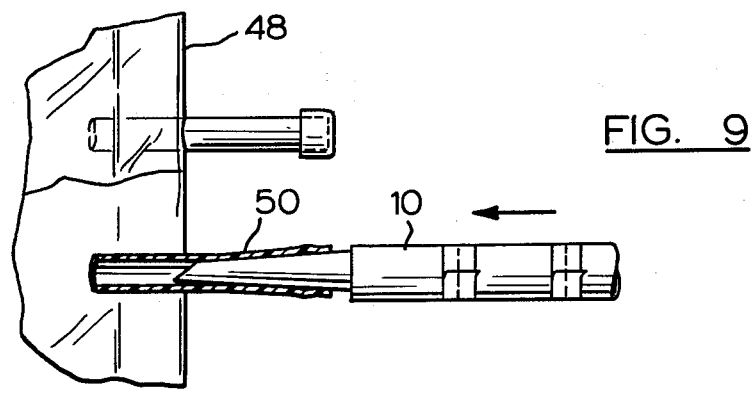

In FIG. 1 of the drawings, there is illustrated two similar tubular needles 10, each designed such that the front end of either of them can be projected into the back end of the other. Also illustrated is a needle 12 the front end of which can be projected into the back end of either of the needles 10 and the back end of which is designed for connection to a plastic or similar liquid supply tube. A protective cap 14 is designed to extend over the front end of any of the needles 10.

The components illustrated in FIG. 1 are shown in a telescoped assembly in FIG. 2. It will be noted that the elongated tubular body of the needles 10 is formed with a through passage and that the through passage of the body adjacent its back end has a cross-section greater than the cross section of the body adjacent its front end whereby the tubular needles 10 can be telescoped into each other by projecting the front end of one of them into the back end of the other as illustrated in FIG. 2.

The outside wall of the body of one of the needles 10 seats on the inside wall of the other needle 10 adjacent the front end thereof in fluid tight relation to limit the projection of the two needles together. Only two needles 10 have been illustrated in FIG. 2 but it will be appreciated that any practical number of similar needles 10 could be telescoped together into an assembly similar to that illustrated in FIG. 2.

The needle 12 has a front end similar to the needles 10 and can be projected into the back end of either of the needles 10 into a fluid tight relation. The difference between needle 12 and needles 10 is that needle 12 is formed with a neck 16 at its back end which is designed to fit into the open end of a feed tube 18 whereby to connect the aligned through passages of the needles to the tube 16.

Cap 14 is adapted to be projected over the front end of a needle 10 as a protective cover for the purpose to be described later.

The needles telescope with respect to each other and seat in fluid tight relation with a press fit.

FIG. 3 illustrates a needle of somewhat different form but of the same essential characteristics. In the case of the needle 20 of FIG. 3, the outer surface is formed with a collar 22 which is adapted for easy manual manipulation as the needles are projected into and out of telescoping relation. Needle 24 is similar in function to needle 12 and cap 26 is similar in function and construction to cap 14.

FIG. 4 is an illustration of a fitting 28 that is adapted to be connected at its end 30 to a tube and which is formed at its other end with an opening to receive the front end of a needle 20. It is used when one desires to connect several series of tubular needles into a common supply line in the manner of FIG. 6.

FIG. 6 is an illustration of three series of needles similar in design to those illustrated in FIGS. 1 and 2 interconnected by short flexible tubes 30 and 32. The tube 30 connects at each end with a fitting 34 which is similar in function to the fitting 28 of FIG. 4 and is adapted to receive in telescoped relation a tubular needle 10.

The tube 36 has a fitting 38 at one end thereof and in use is adapted for connection to a catheter permanently mounted in the body of a patient when the needles are used in a peritoneal dialysis technique to be described.

The space between the back end of the needles 10 and the shoulder of an adjacent needle when they are in fluid tight telescoped relation, as illustrated in FIG. 2, is covered by means of a tape 40 the free end of which can be manually gripped so that a person can selectively peal the tape from the telescoped assembly of tubular needles. Alternative means for preventing seperation until required will be apparent to those skilled in the art.

Figure 10:
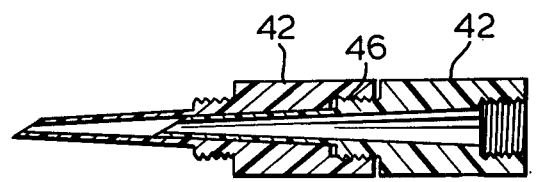
FIG. 10 is a cross sectional illustration of an alternative needle design.

FIG. 10 is a still further embodiment of a tubular needle wherein the telescoped needles 42 have a threadedly engaging extent 46 that can be tightened to cause the outside wall of the back needle to seat on the inside wall of the foreward needle as viewed in FIG. 10. Tightening of the threaded engagement gives a secure and positive seating of the needles.

As indicated in the preamble to this specification, this invention is of use in the practice of a dialysis technique known as continuous ambulatory peritoneal dialysis for persons who have suffered kidney failure.

In accordance with this technique, a dialysate is transferred from a plastics material bag to the peritoneal cavity, permitted to remain there for a period of about six hours and then drained from the peritoneal cavity. After draining a fresh bag of dialysate is conducted to the peritoneal cavity.

The technique, apparently, is a superior technique to known methods of dialysis for patients who have suffered kidney failure and one of its advantages is that the patient can attend to the changing of the dialysate himself. A serious difficulty with the technique, however, is the danger of infection as the patient changes the dialysate. Under normal conditions, the dialysate must be changed four times a day and it is not an easy matter for the patient to maintain the connections between the dialysate container and the tube that leads from the container to the permanently embedded catheter on his body in a satisfactory sterile condition.

This invention provides a tubular needle that will assist patients to maintain the required degree of sterility of the connectors between the dialysate bag and the tube that conducts the dialysate from the bag to the peritoneal cavity.

Consider the assembly illustrated in FIG. 6. It consists of three series of telescoped needles 10 joined by short lengths of tube 30 and 32 with a cap 14 over the exposed end needle 10, and a long tube 36 connected to the fitting 12 of the upper series of needles. Each series of needles has four needle points. The free end 38 of the long tube 36 is connected to a cathether that is permanently implanted in the abdomen of the patient and that extends into the peritoneal cavity. This connection would be made by trained medical personel or by a patient after a period of training. The tube 36 and its interconnected nozzles can now be used to admit dialysate to the peritoneal cavity and to drain dialysate from the peritoneal cavity.

To admit dialysate to the peritoneal cavity, one would first remove the cap 14 from the front end of the left hand needle 10 of the lower series of needles illustrated in FIG. 6. The cap has previously covered the front end of the needle to maintain its sterility so that the needle that is exposed as the cap 14 is withdrawn is sterile. The dialysate is contained in a plastics material bag 48 which has a tubular neck 50 at one end. By projecting the front end of the needle 10 into the tubular neck 50 and breaking the membrane that extends thereacross for the purpose of sealing it, one connects the needle to the container. The container is then mounted on a hook in an upside down position as illustrated in FIG. 7 at a level above the level of the peritoneal cavity of the patient. The dialysate drains from the bag through the series of needles and tube 36 into the peritoneal cavity. When the drainage is completed, the bag is rolled up and inserted into an appropriate purse and strapped to the patient's body above the level of the peritoneal cavity. The patient is then free to move as he pleases while the dialysate absorbs the harmful poisons from his body that must be removed because of his kidney failure.

After a period of about six hours, the dialysate must be removed from the peritoneal cavity and this is done by removing the container 48 from its purse and mounting it on a hook 50 in an upside down position at a level below the level of the peritoneal cavity (dotted lines, FIG. 2) so that the dialysate in the peritoneal cavity can drain back from the peritoneal cavity into the container 48.

When drainage has been completed, the needle 10 that is connected to the container 48 is removed from the container. By this time, the needle has most likely become contaminated and if used with a fresh bag of dialysate would most likely contaminate that bag and result in peritonitis of the patient.

A fresh bag of dialysate must be supplied to the patient and this can be done under sterile conditions by using a fresh needle to connect the bag to the supply tube 36. This is achieved by removing the seal 40 that connects the needle just used to the next following needle in the series and then removing the needle that has just been used from the series. As this is done, a fresh needle is exposed, the front end of which is not contaminated by contact with things exterior of the system. This freshly exposed needle is then connected to the fresh bag of dialysate and the contents of the bag of dialysate is admitted to the patient's peritoneal cavity as before and subsequently drained as before.

The procedure is repeated and each time a fresh bag of dialysate is supplied to the patient a needle with a sterile forward end is used.

It will be noted that in FIG. 6, three series of needles each having four front ends for connection to a dialysate bag have been provided. It will be appreciated that when the last needle in a series has been used, one of the sections of tube 30 or 32, as the case may be, must be removed together with its fitting to expose the front end of a next following needle. The front ends of the needles in the middle series of needles face in the opposite direction to the front ends of the needles in the bottom series and the front ends of the needles in the top series face in the same direction as the front ends of the needles in the bottom series.

There are four needles in each series and a patient normally requires four bags of dialysate a day. Thus, the assembly of needles illustrated in FIG. 6 would last a patent three days.

In the manufacture of the assemblies the needles would be assembled under clean conditions and then subjected to gamma ray radiation to achieve sterility of the assembled parts.

Embodiments and uses of the invention other than the ones illustrated will be apparent to those skilled in the art such as uses involving multiple intravenous solutions. Important is the tubular needle the front end of which can be telescoped into the back end of another similar tubular needle to dispose the outer wall thereof in fluid tight relation with the inner wall of the similar needle for subsequent separation whereby upon separation the front end portion that was telescoped into the back end of the other needle is not contaminated by foreign material upon removal. The specific design of the fit between them is not critical.

The embodiments of the invention in which an exclusive property or privilege is claimed are defined as follows:

1. In combination at least two tubular needles each comprising:
   an elongated body with a through passage;
   said body having an inside wall, an outside wall, a front end and a back end;
   said through passage of said body adjacent said back end of said body having a cross section greater than the cross section of said body adjacent said front end of said body, said tubular needles being telescoped together in a series with the said front end of each needle except the last needle in the series projected into the back end of the next needle in the series;
   said outside wall of said body of each needle being adapted to seat on the inside wall of said body of a needle into which it is projected adjacent the front end thereof in fluid tight relation to limit the projection of said outside wall of said body into said back end of the next needle in the series;
   said outside wall of said body of each of said needles being formed with a shoulder adjacent its back end, the back end of said shoulder extending to said back end of said body and being closely spaced from the front end of the shoulder of a similar needle when said needle is telescoped together in series with other needles as aforesaid;
   a removable seal over the adjacent marginal portions of said shoulder of adjacent needles in said series of needles.

2. In combination at least two tubular needles each comprising:
   an elongated body with a through passage;
   said body having an inside wall, an outside wall, a front end and a back end;
   said through passage of said body adjacent said back end of said body having a cross section greater than the cross section of said body adjacent said front end of said body, said tubular needles being telescoped together in a series with the said front end of each needle except the last needle in the series projected into the back end of the next needle in the series;
   said outside wall of said body of each needle being adapted to seat on the inside wall of said body of a needle into which it is projected adjacent the front end thereof in fluid tight relation to limit the projection of said outside wall of said body into said back end of the next needle in the series;
   means that is manually removable for preventing their separation of said needles from said series arrangement of needles until removed.

3. In combination at least two tubular needles each comprising:
   an elongated body with a through passage;
   said body having an inside wall, an outside wall, a front end and a back end;
   said through passage of said body adjacent said back end of said body having a cross section greater than the cross section of said body adjacent said front end of said body, said tubular needles being telescoped together in a series with the said front end of each needle except the last needle in the series projected into the back end of the next needle in the series;
   said outside wall of said body of each needle being adapted to seat on the inside wall of said body of a needle into which it is projected adjacent the front end thereof in fluid tight relation to limit the projection of said outside wall of said body into said back end of the next needle in the series;
   said outside wall of said body of each of said needles being formed with a shoulder adjacent its back end, the back end of said shoulder extending to said back end of said body and being closely spaced from the front end of the shoulder of a similar needle when said needle is telescoped together in series with other needles as aforesaid;
   means that is manually removable for preventing separation of said needle from said series arrangement of needles until removed.

4. In combination at least two tubular needles each comprising;
   an elongated body with a through passage;
   said body having an inside wall, an outside wall, a front end and a back end;
   said through passage of said body adjacent said back end of said body having a cross section greater than the cross section of said body adjacent said front end of said body, said tubular needles being telescoped together in a series with the said front end of each needle except the last needle in the series projected into the back end of the next needle in the series;
   said outside wall of said body of each needle being adapted to seat on the inside wall of said body of a needle into which it is projected adjacent the front end thereof in fluid tight relation to limit the projection of said outside wall of said body into said back end of the next needle in the series;
   said outside wall of said body of each of said needles being formed with a shoulder adjacent its back end, the back end of said shoulder extending to said back end of said body and being closely spaced from the front end of the shoulder of a similar needle when said needle is telescoped together in series with other needles as aforesaid;
   a removable seal over the adjacent marginal portions of said shoulder of adjacent needles in said series of said needles, manually removable means covering the front exterior portion of the front needle of said series, a tube and means connecting the back needle in said series to one end of said tube.

5. In combination at least two tubular needles each comprising;
   an elongated body with a through passage;
   said body having an inside wall, an outside wall, a front end and a back end;
   said through passage of said body adjacent said back end of said body having a cross section greater than the cross section of said body adjacent said front end of said body, said tubular needles being telescoped together in a series with the said front end of each needle except the last needle in the series projected into the back end of the next needle in the series;

said outside wall of said body of each needle being adapted to seat on the inside wall of said body of a needle into which it is projected adjacent the front end thereof in fluid tight relation to limit the projection of said outside wall of said body into said back end of the next needle in the series;

means that is manually removable for preventing separation of said needles from said series arrangement of needles until removed, manually removable means covering the front exterior portion of the front needle of said series, a tube and means connecting the back needle in said series to one end of said tube.

6. In combination at least two tubular needles each comprising;

an elongated body with a through passage;

said body having an inside wall, an outside wall, a front end and a back end;

said through passage of said body adjacent said back end of said body having a cross section greater than the cross section of said body adjacent said front end of said body, said tubular needles being telescoped together in a series with the said front end of each needle except the last needle in the series projected into the back end of the next needle in the series;

said outside wall of said body of each needle being adapted to seat on the inside wall of said body of a needle into which it is projected adjacent the front end thereof in fluid tight relation to limit the projection of said outside wall of said body into said back end of the next needle in the series;

said outside wall of said body of each of said needles being formed with a shoulder adjacent its back end, the back end of said shoulder extending to said back end of said body and being closely spaced from the front end of the shoulder of a similar needle when said needle is telescoped together in series with other needles as aforesaid;

means that is manually removable for preventing separation of said needles from said series arrangement of needles until removed, manually removable means covering the front exterior portion of the front needle of said series, a tube and means connecting the back needle in said series to one end of said tube.

* * * * *